(12) United States Patent
Aota et al.

(10) Patent No.: US 11,642,446 B2
(45) Date of Patent: May 9, 2023

(54) BLOOD PURIFICATION SYSTEM (71) Applicant: Nikkiso Company Limited, Tokyo (JP)

(72) Inventors: Naoyuki Aota, Shizuoka (JP);
Masahiro Toyoda, Shizuoka (JP);
Yasunobu Hagiwara, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 313 days.

(21) Appl. No.: 16/711,713

(22) Filed: Dec. 12, 2019

(65) Prior Publication Data
US 2020/0114055 A1    Apr. 16, 2020

Related U.S. Application Data (63) Continuation of application No. PCT/JP2018/022702, filed on Jun. 14, 2018.

(30) Foreign Application Priority Data

Jun. 14, 2017  (JP) .............................. JP2017-116953

(51) Int. Cl.
G16H 20/40     (2018.01)
G16H 10/60     (2018.01)
(Continued)

(52) U.S. Cl.
CPC .......... A61M 1/1603 (2014.02); A61M 1/267 (2014.02); A61M 1/3403 (2014.02);
(Continued)

(58) Field of Classification Search
CPC .............................. G16H 10/60; G16H 15/00
See application file for complete search history.

(56) References Cited

U.S. PATENT DOCUMENTS

2004/0057037 A1*  3/2004  Ohishi .................... A61M 1/16
                                                           356/39
2004/0111293 A1*  6/2004  Firanek .................. G16H 40/20
                                                           705/2
(Continued)

FOREIGN PATENT DOCUMENTS

EP         1908486 A1    4/2008
JP    2007-289481 A    11/2007
(Continued)

OTHER PUBLICATIONS

European Search Report for Application No. 18816897.5, dated Feb. 10, 2021.

*Primary Examiner* — Robert A Sorey
*Assistant Examiner* — Kristine K Rapillo
(74) *Attorney, Agent, or Firm* — Young Basile Hanlon & MacFarlane, P.C.

(57) ABSTRACT

A blood purification system is provided that is capable of effectively utilizing accumulated histories stored during blood purification treatment and that helps take a quick and appropriate action in response to a particular incident that occurs unsteadily. In a blood purification system, a history stored in a storage device includes particular incidents having occurred unsteadily in blood purification treatment. The blood purification system includes an extracting device capable of searching the histories accumulated in the storage device and extracting a desired one of the particular incidents, a calculating device capable of calculating a time when the particular incident extracted by the extracting device occurs a predetermined or more number of times as a frequent-occurrence time slot, and a display control device capable of displaying the frequent-occurrence time slot calculated by the calculating device on a display during a current session of blood purification treatment.

18 Claims, 8 Drawing Sheets

(51) Int. Cl.
*G16H 15/00* (2018.01)
*A61M 1/16* (2006.01)
*A61M 1/26* (2006.01)
*A61M 1/34* (2006.01)
*A61M 1/36* (2006.01)

(52) U.S. Cl.
CPC .......... *A61M 1/3639* (2013.01); *G16H 10/60* (2018.01); *G16H 15/00* (2018.01); *G16H 20/40* (2018.01); *A61M 2205/3569* (2013.01); *A61M 2205/50* (2013.01); *A61M 2205/502* (2013.01); *A61M 2205/505* (2013.01); *A61M 2205/52* (2013.01); *A61M 2205/587* (2013.01)

(56) References Cited

U.S. PATENT DOCUMENTS

| | | | | |
|---|---|---|---|---|
| 2005/0102165 A1* | 5/2005 | Oshita | .................... | G16H 10/40 |
| | | | | 705/3 |
| 2011/0004085 A1* | 1/2011 | Mensinger | ........... | A61B 5/7275 |
| | | | | 600/365 |
| 2013/0300961 A1* | 11/2013 | Tomikawa | .......... | G02F 1/13306 |
| | | | | 349/33 |
| 2013/0303961 A1* | 11/2013 | Wolff | ...................... | A61M 1/16 |
| | | | | 604/5.04 |

FOREIGN PATENT DOCUMENTS

| | | |
|---|---|---|
| JP | 2014-004194 A | 1/2014 |
| WO | 2013/173349 A2 | 11/2013 |
| WO | 2016/113069 A1 | 7/2016 |

\* cited by examiner

BLOOD PURIFICATION SYSTEM

FIELD

The present invention relates to a blood purification system including a blood purification apparatus capable of giving blood purification treatment to a patient, and a managing apparatus capable of communicating with the blood purification apparatus in such a manner as to transmit and receive information on the blood purification treatment to and from the blood purification apparatus.

BACKGROUND

A dialysis apparatus as a blood purification apparatus is used in dialysis treatment or the like. A dialysis room in a medical facility such as a hospital is provided with a plurality of dialysis apparatuses so that dialysis treatment (blood purification treatment) can be given to many patients in the dialysis room. As disclosed by PTL 1 for example, each of such dialysis apparatuses is connected to a central monitoring apparatus (a managing apparatus) including a server, and is capable of receiving various pieces of information on patients that are stored in the server. In recent cases, pieces of information on dialysis treatment (for example, patients' past treatment data and so forth) are stored in the server of the central monitoring apparatus, and any of those pieces of information is displayed on a display according to need so that a medical worker such as a doctor can grasp the information.

PTL 1: Japanese Unexamined Patent Application Publication No. 2014-4194 the teachings of which are incorporated by reference herein for all purposes.

SUMMARY

Such a known blood purification system can display information accumulated in the server and can make the medical worker or the like grasp the information. However, there has been a problem that making an appropriate and quick action during the treatment in response to the information requires a certain level of skill. For example, although any particular incident that has occurred unsteadily during a certain treatment session is stored in the server, simply displaying the particular incident in subsequent treatment sessions cannot help grasp at what frequency or with what timing the particular incident tends to occur. Therefore, if the same particular incident actually occurs, it may be difficult to take a quick and appropriate action.

The present invention has been conceived in view of the above circumstances and provides a blood purification system that is capable of effectively utilizing accumulated histories stored during blood purification treatment and that helps take a quick and appropriate action in response to a particular incident that occurs unsteadily.

According to the teachings herein, there is provided a blood purification system comprising a blood purification apparatus capable of giving blood purification treatment to a patient; a managing apparatus capable of communicating with the blood purification apparatus in such a manner as to transmit and receive information on the blood purification treatment to and from the blood purification apparatus, the managing apparatus including a storage device capable of storing the information on the blood purification treatment in a time course with the progress of the treatment and accumulating the information as a history for each treatment session; and a display provided to the blood purification apparatus or to the managing apparatus and being capable of displaying the information on the blood purification treatment. The history includes particular incidents having occurred unsteadily in the blood purification treatment. The blood purification system includes an extracting device capable of searching the histories accumulated in the storage device and extracting a desired one of the particular incidents, a calculating device capable of calculating a time when the particular incident extracted by the extracting device occurs a predetermined or more number of times as a frequent-occurrence time slot, and a display control device capable of displaying the frequent-occurrence time slot calculated by the calculating device on the display during a current session of blood purification treatment.

According to the teachings herein, in the blood purification system taught herein, the particular incidents include an unsteady incident related to a patient's behavior during the blood purification treatment or an unsteady incident related to a patient's condition, or an unsteady incident occurring in the apparatus during the blood purification treatment.

According to the teachings herein, in the blood purification system taught herein, the display control device is capable of displaying information on the current session of blood purification treatment as a graph with progress of time, and is capable of displaying the frequent-occurrence time slot calculated by the calculating device with reference to a time axis of the graph.

According to the teachings herein, in the blood purification system taught herein, the display control device is capable of displaying the frequent-occurrence time slot calculated by the calculating device as a band graph represented with reference to the time axis.

According to the teachings herein, the blood purification system taught herein further includes an input device that accepts selective input of any of the plurality of particular incidents. The calculating device calculates the frequent-occurrence time slot of the particular incident inputted through the input device.

According to the teachings herein, in the blood purification system taught herein, in a case where a plurality of particular incidents are inputted through the input device, the display control device is capable of displaying the frequent-occurrence time slots of the plurality of particular incidents such that kinds of the particular incidents are identifiable.

According to the teachings herein, in the blood purification system taught herein, the display control device is capable of displaying the frequent-occurrence time slot such that a frequency of occurrence of the particular incident is identifiable.

According to the teachings herein, the blood purification system includes the extracting device capable of searching the histories accumulated in the storage device and extracting a desired one of the particular incidents, the calculating device capable of calculating the time when the particular incident extracted by the extracting device occurs a predetermined or more number of times as a frequent-occurrence time slot, and the display control device capable of displaying the frequent-occurrence time slot calculated by the calculating device on the display during the current session of blood purification treatment. Therefore, the medical worker can grasp the frequent-occurrence time slot of the particular incident in advance. Hence, the accumulated histories stored during the blood purification treatment can be utilized effectively, and an action in response to the particular incidents that occur unsteadily can be taken quickly and appropriately.

According to the teachings herein, the particular incidents include an unsteady incident related to the patient's behavior during the blood purification treatment or an unsteady incident related to the patient's condition, or an unsteady incident occurring in the apparatus during the blood purification treatment. Therefore, the medical worker can grasp the frequent-occurrence time slots of various particular incidents in advance.

According to the teachings herein, the display control device is capable of displaying information on the current session of blood purification treatment as a graph with the progress of time, and is also capable of displaying the frequent-occurrence time slot calculated by the calculating device with reference to the time axis of the graph. Therefore, the information on the current session of blood purification treatment and the frequent-occurrence time slot can be compared visually.

According to the teachings herein, the display control device is capable of displaying the frequent-occurrence time slot calculated by the calculating device as a band graph represented with reference to the time axis. Therefore, the comparison between the information on the current session of blood purification treatment and the frequent-occurrence time slot can be made more smoothly and visually.

According to the teachings herein, the blood purification system includes the input device that accepts selective input of any of the plurality of particular incidents. Furthermore, the calculating device calculates the frequent-occurrence time slot of the particular incident inputted through the input device. Therefore, the frequent-occurrence time slot of any desired particular incident can be selectively displayed.

According to the teachings herein, in a case where a plurality of particular incidents are inputted through the input device, the display control device is capable of displaying the frequent-occurrence time slots of the plurality of particular incidents such that the kinds thereof are identifiable. Therefore, the frequent-occurrence time slots of a plurality of desired particular incidents can be displayed simultaneously.

According to the teachings herein, the display control device is capable of displaying the frequent-occurrence time slot such that the frequency of occurrence of the particular incident is identifiable. Therefore, an action suitable for the frequency of occurrence of each of the particular incidents can be taken.

DETAILED DESCRIPTION

Embodiments of the present invention will now be described specifically with reference to the drawings.

Figure 1:
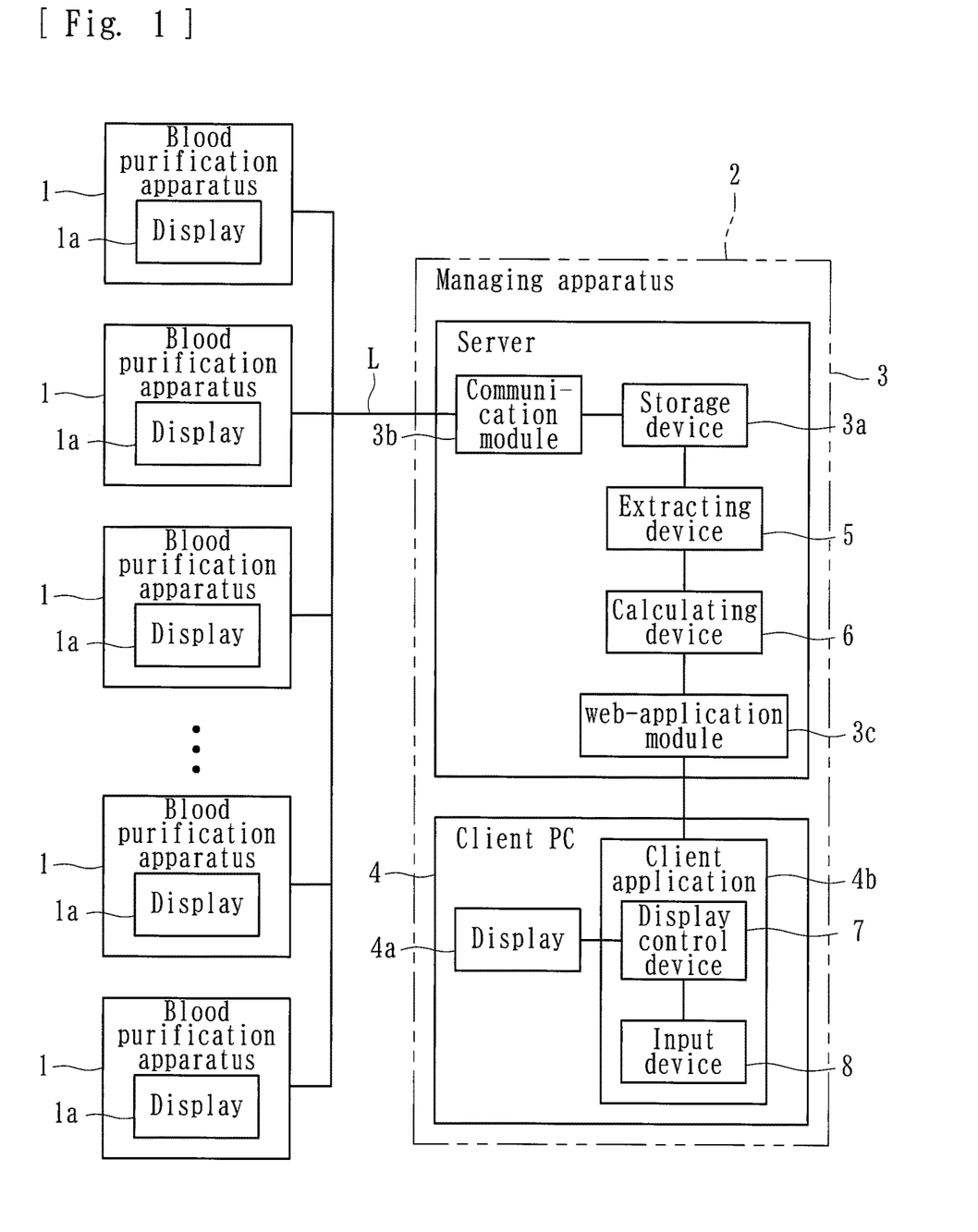
FIG. 1 is a block diagram of a blood purification system according to a first embodiment of the present invention.

A blood purification system according to a first embodiment is capable of giving dialysis treatment as blood purification treatment to patients and includes, as illustrated in FIG. 1, blood purification apparatuses 1 and a managing apparatus 2. The blood purification apparatuses 1 and the managing apparatus 2 are electrically connected to each other through LAN cables (L). Hence, the blood purification apparatuses 1 and the managing apparatus 2 can communicate with each other in such a manner as to transmit and receive information on the blood purification treatment to and from each other.

Figure 3:
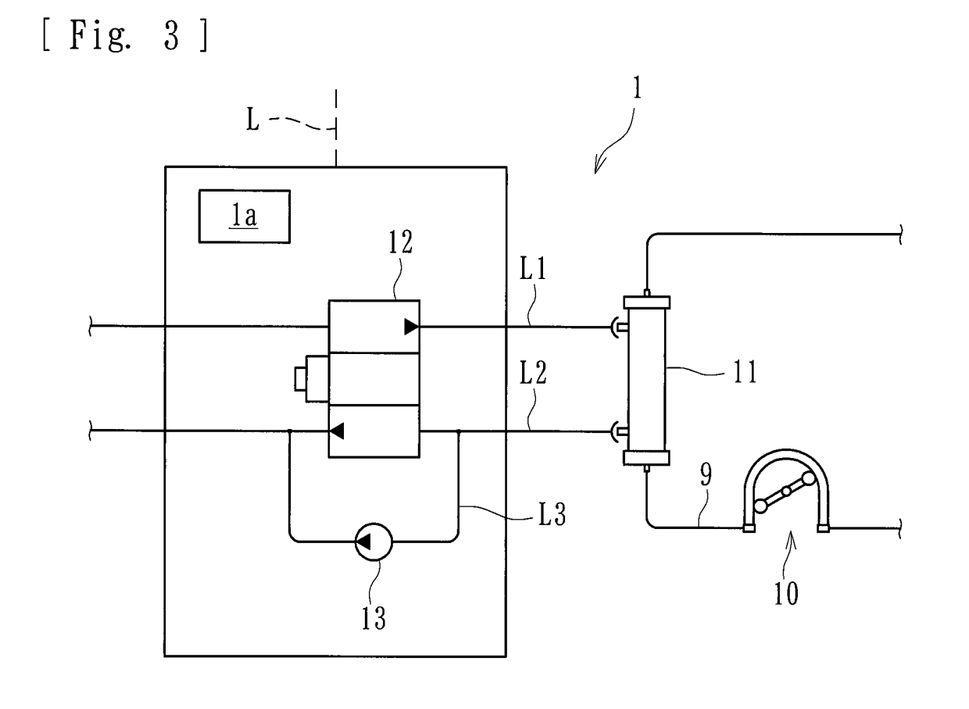
FIG. 3 is a schematic diagram illustrating an internal configuration and a blood circuit of the blood purification apparatus included in the blood purification system.

As illustrated in FIG. 3, each of the blood purification apparatuses 1 includes a dialysate introduction line L1 for introducing dialysate, a dialysate drain line L2 through which waste dialysate is drained, and a duplex pump 12 provided over the dialysate introduction line L1 and the dialysate drain line L2. A dialyzer 11 (a blood purifier) is connected to the dialysate introduction line L1 and to the dialysate drain line L2. A blood circuit 9 through which blood of a patient is caused to extracorporeally circulate is connected to the dialyzer 11. When a blood pump 10 is activated, the blood of the patient is caused to extracorporeally circulate through the blood circuit 9 and can be purified by the dialyzer 11.

A pump chamber of the duplex pump 12 is divided by a single plunger, not illustrated, into a delivery-side pump chamber connected to the dialysate introduction line L1 and a drain-side pump chamber connected to the dialysate drain line L2. When the plunger undergoes a reciprocal motion, the dialysate or a cleaning solution delivered to the delivery-side pump chamber is supplied to the dialyzer 11, while the dialysate in the dialyzer 11 is taken into the drain-side pump chamber.

The dialysate drain line L2 is provided with a bypass line L3 that bypasses the duplex pump 12. The bypass line L3 is provided with an ultrafiltration pump 13 at a halfway position thereof. When the ultrafiltration pump 13 is activated, the blood of the patient that is flowing in the dialyzer 11 can be ultrafiltered. The duplex pump 12 may be replaced with a device of a so-called chamber type.

The blood purification apparatus 1 further includes a display 1a and various treatment devices (for example, the blood pump, an infusion pump, a syringe pump, and so forth) related to blood purification treatment (hemodialysis treatment). The treatment devices are not limited to actuators such as pumps and may include various general devices intended for blood purification treatment: namely, clamping devices such as electromagnetic valves, and monitoring devices for monitoring hydraulic pressure and so forth.

The display 1a is capable of displaying predetermined information on the blood purification treatment (hemodialysis treatment) and accepts predetermined input. The display 1a according to the present embodiment is a touch panel that accepts predetermined input made by touching on a desired one of positions of a screen thereof. The information on the blood purification treatment that is displayed on the display 1a includes a setting value representing the flow rate of the blood pump 10, the ultrafiltration pump 13, the infusion pump, or the like; the venous pressure detected by a venous pressure sensor; and the hematocrit value or the like detected by a hematocrit sensor or the like.

Figure 2:
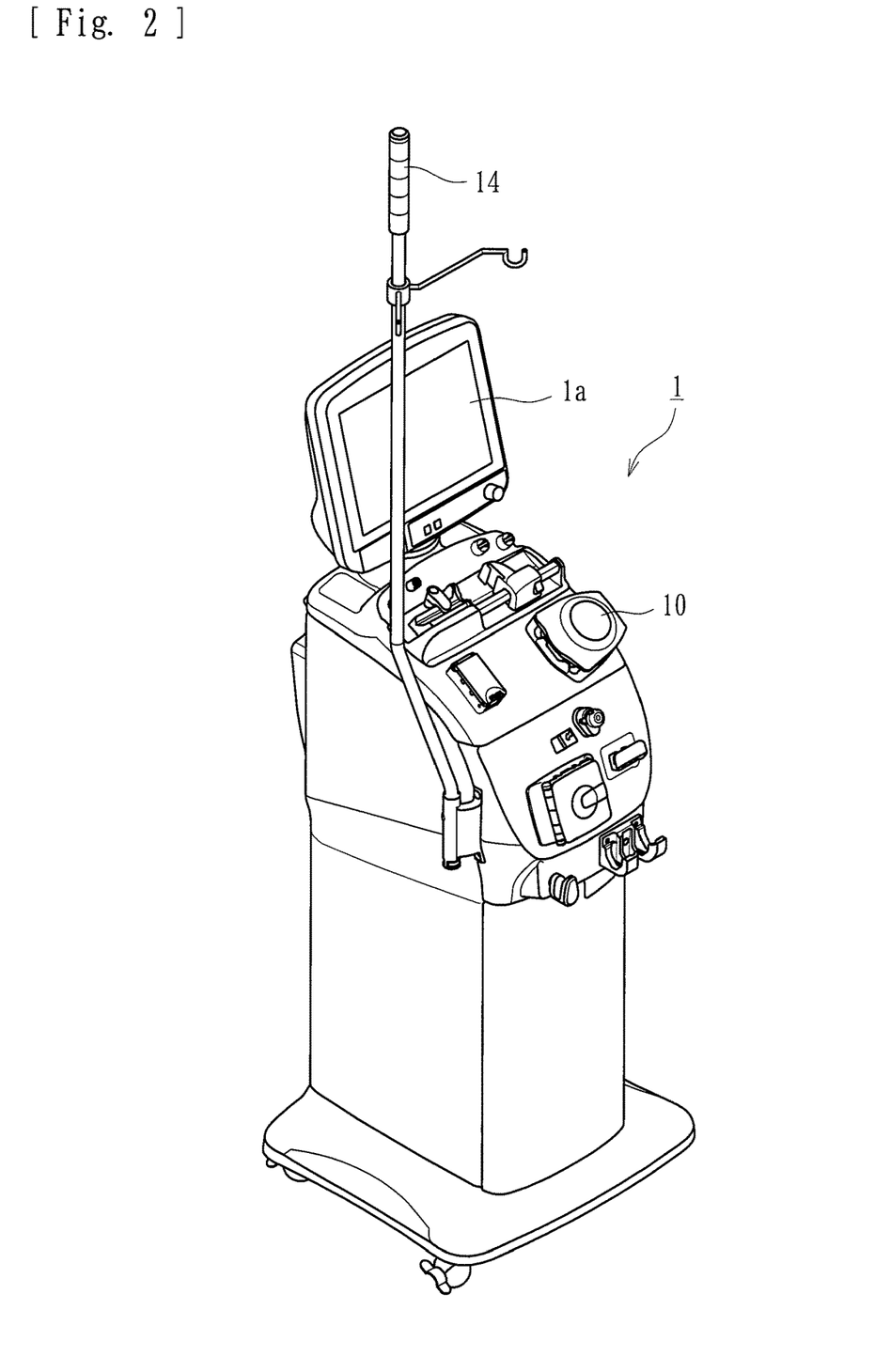
FIG. 2 is a diagram illustrating an appearance of a blood purification apparatus included in the blood purification system.

The blood purification apparatus 1 further includes a speaker capable of generating any type of output (output such as a voice or a sound effect). The speaker makes it possible to generate an alarm or a warning for notifying anyone nearby of the occurrence of an abnormality in any of the devices operating for the blood purification treatment or in the patient, and to give the operator a guidance, with a voice or the like, on how to handle the blood purification apparatus or how to make various settings. The blood purification apparatus 1 further includes an external indicator lamp 14 (see FIG. 2). The external indicator lamp 14 is turned on or is made to blink, so that anybody nearby can notice the warning or the like more assuredly.

The managing apparatus 2 includes a server 3 and a client PC 4. The server 3 includes a communication module 3b for communication with the blood purification apparatuses 1 through the LAN cables (L), a storage device 3a serving as a database in which data is accumulatable, a web-application module 3c that activates a client application 4b included in the client PC 4, an extracting device 5, and a calculating device 6. The client PC 4 is provided in a treatment room in which the blood purification apparatuses 1 are installed. The server 3 is provided in another room (such as a computer room) separate from the treatment room.

The storage device 3a is capable of communicating with each of the blood purification apparatuses 1 through the communication module 3b. The storage device 3a is also capable of storing information on the blood purification treatment in a time course with the progress of the treatment and accumulating the information as a history for each treatment session. For example, information transmitted from the managing apparatus 2 to each blood purification apparatus 1 (information required for the current treatment session) includes setting information on the blood purification apparatus 1, master information that enables selection of a below-described particular incident that has occurred unsteadily, personal information (such as dry weight (DW), medication instructions, and test values) on the patient to be treated, and so forth.

Information (the history) transmitted from each blood purification apparatus 1 to the managing apparatus 2 includes monitoring information on the blood purification apparatus 1, warnings and notifications generated by the blood purification apparatus 1, a record of actions including a log of operations performed in response to the warnings and notifications, self-diagnostic information on the blood purification apparatus 1, information on the patient's blood pressure and pulse measured by a blood pressure monitor provided to the blood purification apparatus 1, information on the patient's temperature inputted to the blood purification apparatus 1 by the operator, identification codes selected from the master information by the medical worker, and so forth.

The history includes particular incidents that have occurred unsteadily (suddenly) during the blood purification treatment. The particular incidents include, for example, unsteady incidents related to the patient's behavior during the blood purification treatment (events such as food taking, the release of the patient for a bathroom break, and a change in body position; sudden incidents such as dislodgement of a puncture needle; and the like) or unsteady incidents related to the patient's condition (a drop in blood pressure, complaints such as feelings of discomfort and itching, and the like), or unsteady incidents occurring in the apparatus during the blood purification treatment (actions taken in response to warnings and notifications generated by the blood purification apparatus 1, and the like).

The storage device 3a is capable of associating various pieces of information with one another and accumulating the pieces of information as a history for each treatment session. The pieces of information to be associated with one another include the particular incidents having occurred unsteadily, the name of the patient treated, the place of treatment, the blood purification apparatus used, information transmitted and received to and from the blood purification apparatus 1 during the treatment, actual values such as the patient's body weight before and after the treatment and the volume and rate of ultrafiltration, treatment conditions, the record of medicines given during the treatment, the record of medical materials used for the treatment, the record of care, and so forth.

Any particular incident can be inputted during the blood purification treatment by selecting the kind thereof (whether it is an event during the treatment, a complaint from the patient, an action taken, or the like) through the display 1a (the touch panel) of the blood purification apparatus 1 or through an input device 8 included in the client application 4b. In the present embodiment, the particular incidents are mastered with identification codes that are classified by kind. If a medical worker wants to input a certain particular incident, the medical worker can select, by inputting, an identification code corresponding to the particular incident of interest and then input the actual particular incident. Hence, the storage device 3a can store particular incidents on the basis of the identification codes.

The warnings and notifications generated by the blood purification apparatus 1 during the blood purification treatment and the record of actions including the log of operations performed in response to the warnings and notifications are also mastered with identification codes that are classified by kind. If a medical worker wants to input a certain particular incident, the medical worker can select, by inputting, an identification code corresponding to the particular incident of interest and then input the actual particular incident.

Figure 4:
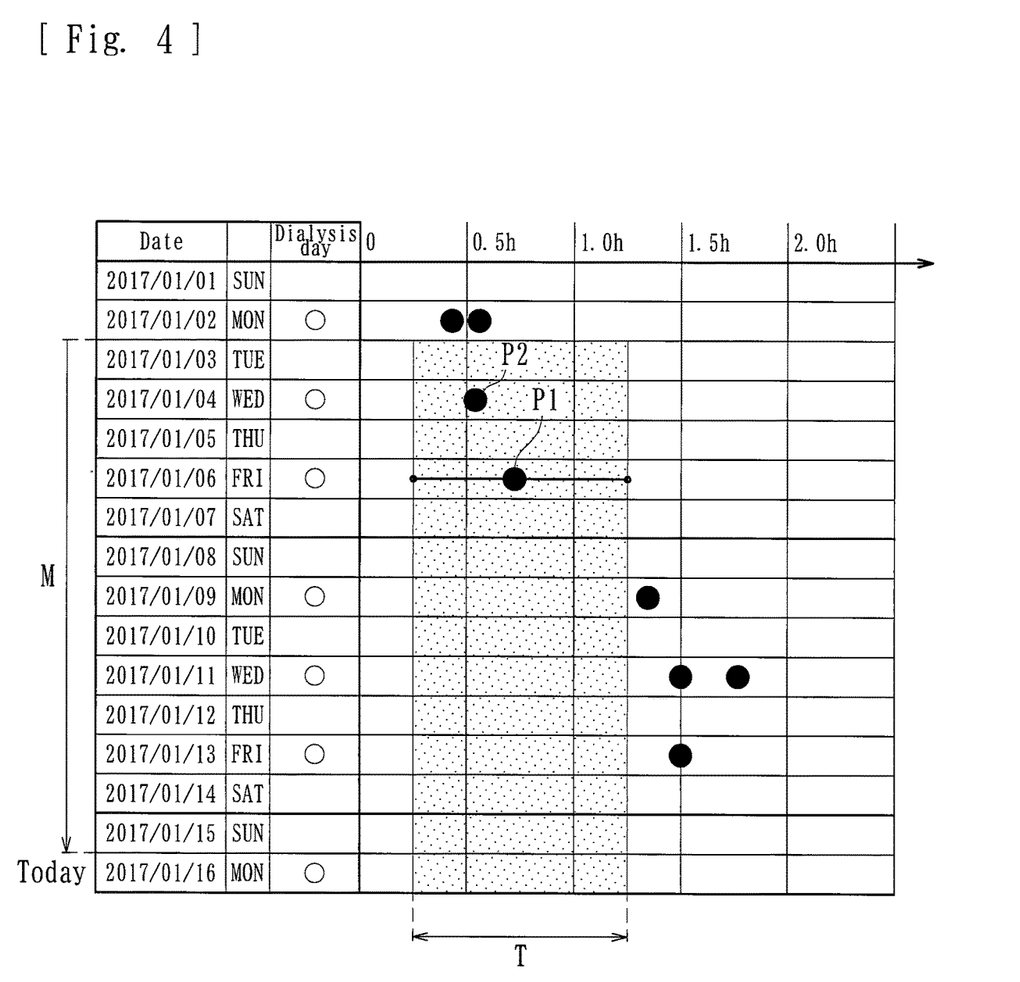
FIG. 4 is a table for describing extraction performed by an extracting device and calculation performed by a calculating device in the blood purification system.
Figure 5:
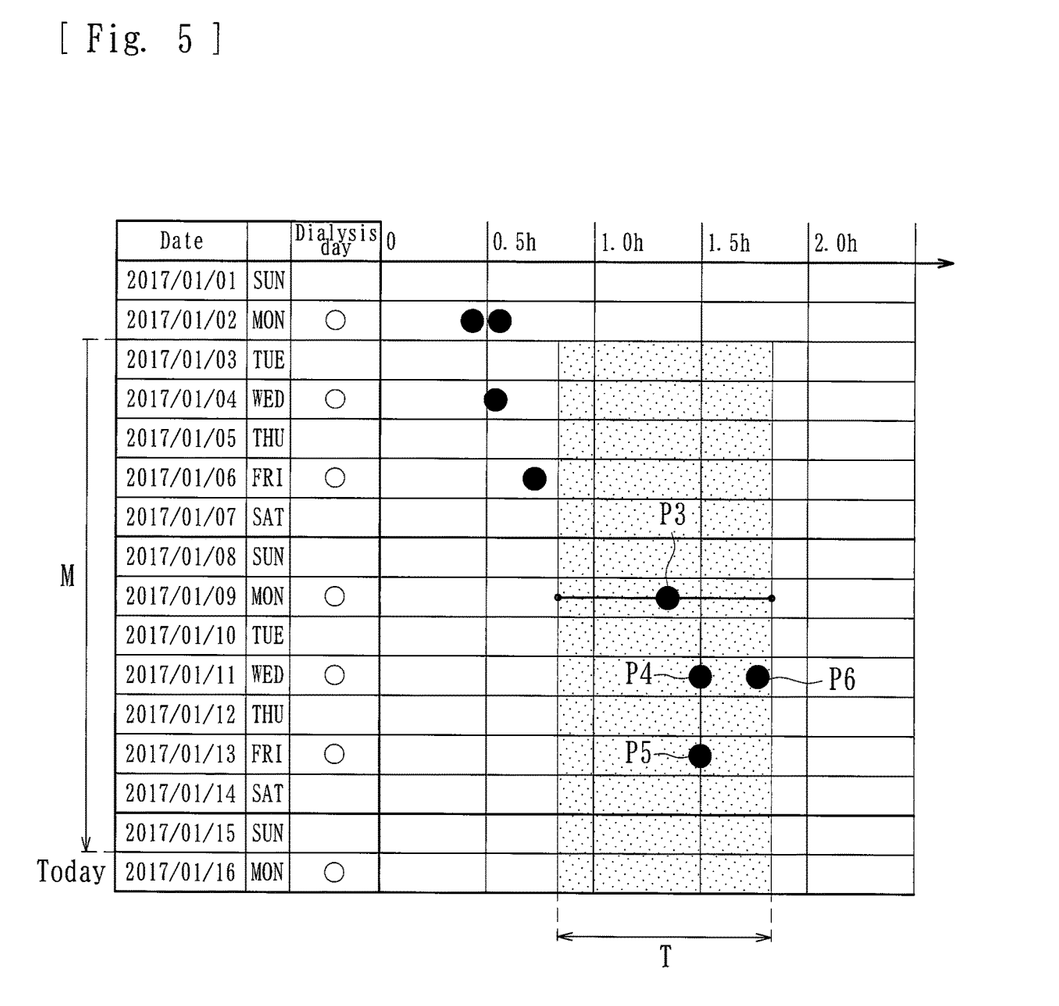
FIG. 5 is a table for describing extraction performed by the extracting device and calculation performed by the calculating device in the blood purification system.
Figure 6:
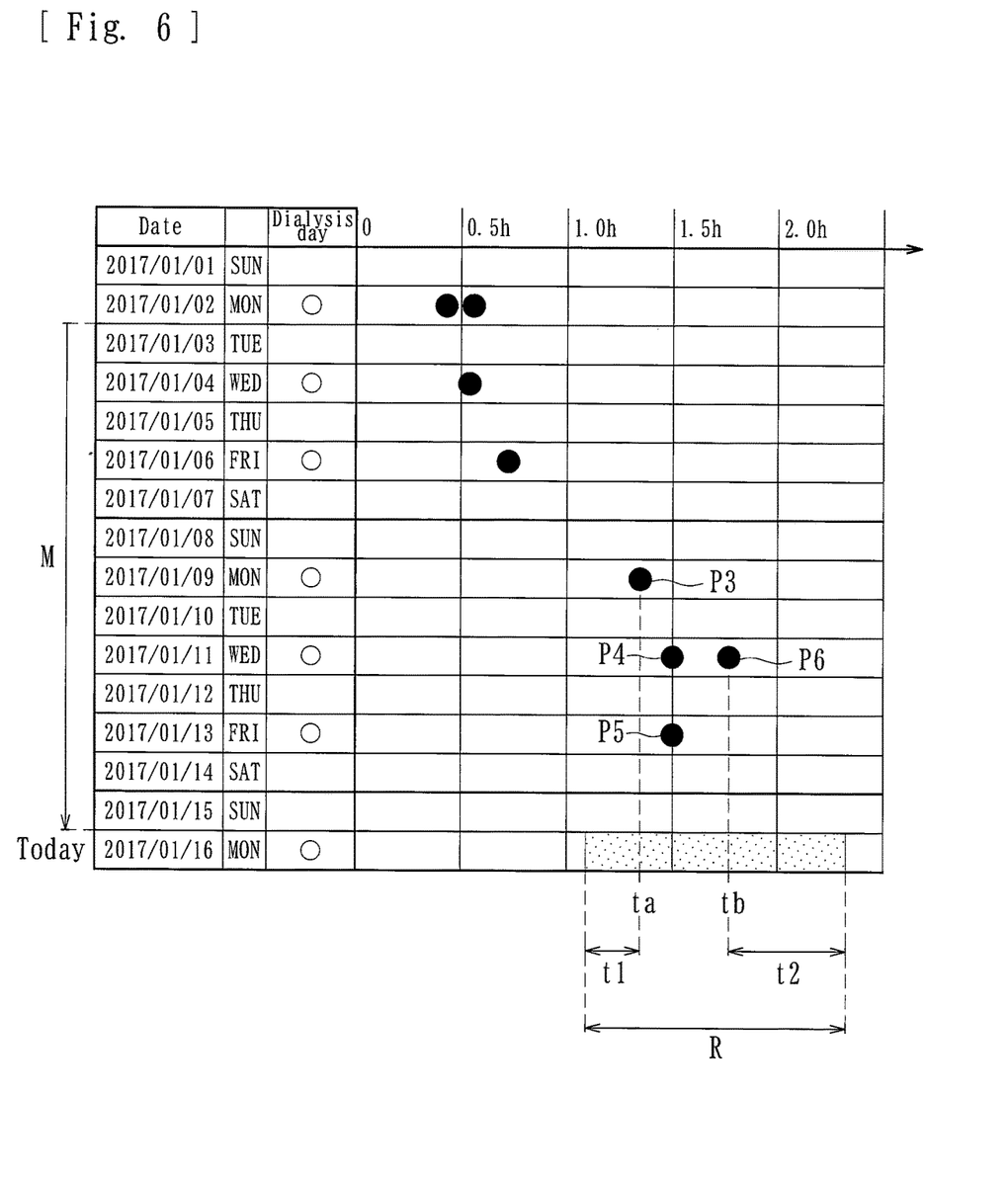
FIG. 6 is a table for describing extraction performed by the extracting device and calculation performed by the calculating device in the blood purification system.

As illustrated in FIGS. 4 to 6, the storage device 3a can store the information on the blood purification treatment in a time course with the progress of the treatment (for example, sequentially from when the patient enters the dialysis room until the patient leaves the dialysis room after the completion of the treatment) and can accumulate the information as a history for each treatment session (each dialysis date). Furthermore, the storage device 3a can store the times of occurrence of the particular incidents on the basis of their kinds and in correspondence with the time in the history. Hence, the storage device 3a can store what kind of particular incident has occurred after how many minutes from the start of a particular one of the past treatment sessions.

The extracting device 5 is capable of searching the histories accumulated in the storage device 3a and extracting a desired one of the particular incidents. When a desired particular incident that needs to be grasped by the medical worker is selected (particular incidents of different kinds are also selectable) and is inputted (specifically, when an identification code corresponding to a desired particular incident is inputted) through the display 1a or the input device 8, the extracting device 5 according to the present embodiment can search the histories stored and accumulated in the storage device 3a and can extract the selected particular incident.

The number of particular incidents to be selected by the medical worker is not limited to one, and a plurality of kinds of particular incidents may be selected and inputted. The kinds of particular incidents to be paid attention to are different for different patients. Therefore, the extraction of such a particular incident by the extracting device 5 may be performed patient by patient.

The present embodiment concerns a case where the range from which the extracting device 5 extracts a particular incident is limited to the histories of the patient to whom the blood purification treatment is going to be given. Alternatively, the extracting device 5 may extract a particular incident from a range including histories of other patients. In the latter case, the other patients acceptable as additional conditions include patients having a similar symptom, patients of the same sex, patients of the same or a close age, patients having the same or a similar primary disease, and patients having the same or a close DW (dry weight) or test value. In addition, the medical worker may arbitrarily include or exclude other patients into or from the range of extraction by the extracting device 5. That is, the medical worker may select patients to be included in the range of extraction for each particular incident.

A particular incident extracted as above is presented as illustrated in FIGS. 4 to 6 in a time course for each of past treatment sessions. Hence, with what timings the particular incident has occurred in the past treatment sessions (dialysis dates) can be grasped. The tables illustrated in the drawings each include lines of dialysis dates arranged vertically in order and columns of treatment time slots (hours) arranged horizontally, with points (dots) of the particular incident of interest plotted with reference to time. The drawings illustrate the result of extraction of a single particular incident. If a plurality of particular incidents are extracted, the result is presented for each of the different kinds of particular incidents in a time course for each of past treatment sessions.

The calculating device 6 is capable of calculating a time when the particular incident extracted by the extracting device 5 occurs a predetermined or more number of times as a frequent-occurrence time slot. For example, as illustrated in FIG. 4, a period (M) is set as an object of calculation. Furthermore, a time slot including slots before and after a particular-incident point P1 among several particular-incident points extracted within the period (M) is defined as a scanning time slot (T). Then, whether the number of particular-incident points extracted within the scanning time slot (T) is greater than or equal to a predetermined value, i.e. a threshold, is checked. The threshold may be set arbitrarily. For example, if the threshold is set to 3 and the number of particular-incident points extracted within the scanning time slot T is 2 (two particular-incident points P1 and P2) as illustrated in the drawing, it is not determined that the occurrence of the particular incident is frequent. The period (M) as the object of calculation can be set arbitrarily by the medical worker or the like and may be set to an indefinite value.

FIG. 5 illustrates a case where a time slot including slots before and after a particular-incident point P3 among several particular-incident points extracted is defined as the scanning time slot (T), and the number of particular-incident points extracted within the scanning time slot (T) is 4 (four particular-incident points P3 to P6). In such a case, it is determined that the occurrence of the particular incident is frequent. Furthermore, as illustrated in FIG. 6, a frequent-occurrence time slot (R) is calculated as a time slot defined between a point before a point ta by an allowance t1 and a point after a point tb by an allowance t2. The point ta corresponds to the particular-incident point P3 as the earliest occurrence in a time course of the treatment session. The point tb corresponds to the particular-incident point P6 as the latest occurrence in a time course of the treatment session.

The client PC 4 is a personal computer and includes a display 4a and the client application 4b. The display 4a is a liquid-crystal screen or a touch panel that is capable of displaying information on the blood purification treatment. The client application 4b is connected to the web-application module 3c of the server 3, whereby information on the blood purification treatment can be inputted thereto and outputted therefrom. The client application 4b includes a display control device 7 and the input device 8.

The input device 8 accepts selective input of any of the plurality of particular incidents (for example, particular incidents of different kinds such as unsteady incidents related to the patient's behavior during the blood purification treatment or unsteady incidents related to the patient's condition, or unsteady incidents occurring in the apparatus during the blood purification treatment). In the present embodiment, the frequent-occurrence time slot of a particular incident inputted through the input device 8 can be calculated by the calculating device 6 and can be displayed by the display control device 7. The input may be made through the display 1a (a touch panel or the like) of the blood purification apparatus 1, instead of the input device 8.

Figure 7:
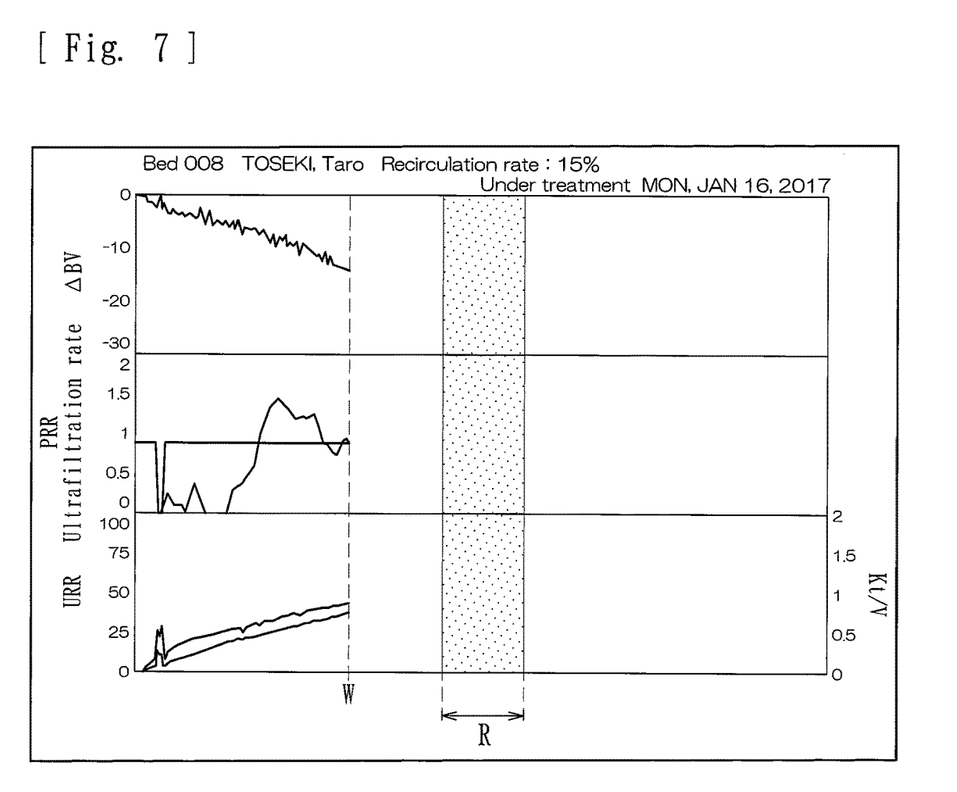
FIG. 7 is a graph illustrating items displayed by a display control device included in the blood purification system.

The display control device 7 is capable of displaying various pieces of information based on the history extracted by the extracting device 5 on the display 4a. In the present embodiment, the display control device 7 is capable of displaying the frequent-occurrence time slot calculated by the calculating device 6 on the display 4a during the current session of blood purification treatment. Specifically, as illustrated in FIG. 7, the display control device 7 according to the present embodiment is capable of displaying pieces of information on the current session of blood purification treatment as graphs with the progress of time (the case illustrated in the drawing includes, with the horizontal axis representing the time axis, a line graph of ΔBV in an upper part, line graphs of PRR and ultrafiltration rate in a middle part, and line graphs of URR and Kt/V in a lower part), and is also capable of displaying the frequent-occurrence time slot (R) calculated by the calculating device 6 with reference to the time axis of the graphs.

In particular, as illustrated in the drawing, the display control device 7 according to the present embodiment is capable of displaying the frequent-occurrence time slot (R) calculated by the calculating device 6 as a band graph represented with reference to the time axis (the time axis of the current session of blood purification treatment). Since the frequent-occurrence time slot R is displayed as a band graph as described above, the start time and the end time of the frequent-occurrence time slot (R) can be grasped simultaneously and visually. Furthermore, about how much time is left from a current time (W) before the frequent-occurrence time slot (R) is reached can be grasped visually.

Figure 8:
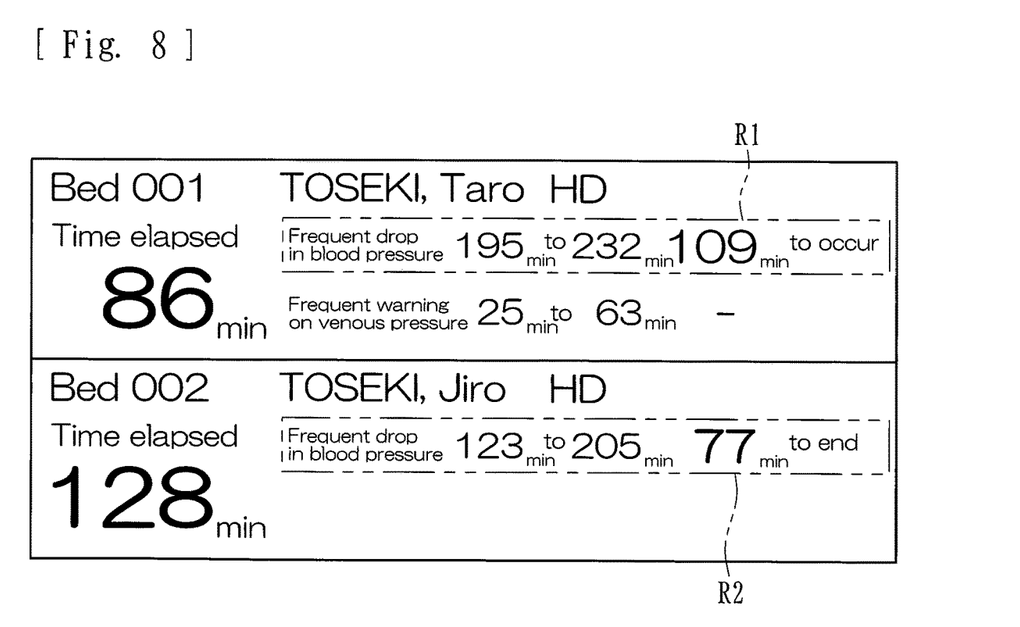
FIG. 8 is a diagram illustrating other items displayed by the display control device included in the blood purification system.

The display control device 7 according to the present embodiment is capable of displaying information on the current session of blood purification treatment as graphs with the progress of time, and is also capable of displaying the frequent-occurrence time slot (R) calculated by the calculating device 6 as a band graph represented with reference to the time axis of the graphs. Alternatively, as illustrated in FIG. 8, the display control device 7 may be capable of displaying the frequent-occurrence time slots (R1, R2) calculated by the calculating device 6 numerically on the display 4a during the current session of blood purification treatment. In the latter case, the frequent-occurrence time slots (R1, R2) is displayed for each of a particular incident of "drop in blood pressure" and a particular incident of "warning on venous pressure". The frequent-occurrence time slots (R1, R2) may be displayed for any other particular incident in any other form.

If a plurality of particular incidents are inputted through the input device 8 (or the display 1a), the display control device 7 may display respective frequent-occurrence time slots such that the kinds of those particular incidents are identifiable. The kinds of the particular incidents can be made identifiable by displaying different frequent-occurrence time slots (represented as graphs or the like) in different colors (including different tones). Moreover, the display control device 7 may display the frequent-occurrence time slots such that the frequencies of occurrence of the respective particular incidents are identifiable. In such a case, frequent-occurrence time slots of higher frequencies and frequent-occurrence time slots of lower frequencies can be made identifiable for each of the particular incidents by displaying the frequent-occurrence time slots (represented as graphs or the like) of different frequencies in different colors (including different tones).

The extraction of a particular incident by the extracting device 5 and the calculation of the frequent-occurrence time slot by the calculating device 6 are preferably performed when the particular incident inputted through the input device 8 is changed, when the recording of the patient's history for each treatment session is completed and determined, or in midnight hours or the like during which the blood purification system is out of operation. Needless to say, if a client PC 4 operating at an extremely high processing speed is employed, the extraction of a particular incident by the extracting device 5 and the calculation of the frequent-occurrence time slot by the calculating device 6 may be performed immediately before the blood purification treatment is started.

According to the above embodiment, the blood purification system includes the extracting device 5 capable of searching the histories accumulated in the storage device 3a and extracting a desired one of the particular incidents, the calculating device 6 capable of calculating the time when the particular incident extracted by the extracting device 5 occurs a predetermined or more number of times as a frequent-occurrence time slot, and the display control device 7 capable of displaying the frequent-occurrence time slot calculated by the calculating device 6 on the display 4a during the current session of blood purification treatment. Therefore, the medical worker can grasp the frequent-occurrence time slot of the particular incident in advance. Hence, the accumulated histories stored during the blood purification treatment can be utilized effectively, and an action in response to the particular incidents that occur unsteadily can be taken quickly and appropriately.

Specifically, the timing of frequent occurrence (the frequent-occurrence time slot) of a desired particular incident that is considered to be paid attention to by the medical worker can be grasped in advance during the current session of blood purification treatment. Therefore, preparations and confirmations for the particular incident of interest can be made in advance, and an action in response to the occurrence of the particular incident can be taken quickly and appropriately. Furthermore, since the frequent-occurrence time slots of the particular incidents can be summarized automatically, not manually by the operator, the number of steps of operation can be reduced. Moreover, since factors such as the threshold for the frequent-occurrence time slot and the scanning time slot (T) can be set arbitrarily on the basis of viewpoints of experienced and high-skill medical workers, even unexperienced and low-skill medical workers can grasp the frequent-occurrence time slots of the particular incidents to be paid attention to.

Note that the particular incidents include unsteady incidents related to the patient's behavior during the blood purification treatment (events such as food taking, the release of the patient for a bathroom break, and a change in body position; sudden incidents such as dislodgement of a puncture needle; and the like) or unsteady incidents related to the patient's condition (a drop in blood pressure, complaints such as feelings of discomfort and itching, and the like), or unsteady incidents occurring in the apparatus during the blood purification treatment (actions taken in response to warnings and notifications generated by the blood purification apparatus 1, and the like). Therefore, the medical worker can grasp the frequent-occurrence time slots of various particular incidents in advance.

Furthermore, the display control device 7 is capable of displaying information on the current session of blood purification treatment as a graph with the progress of time, and is also capable of displaying the frequent-occurrence time slot calculated by the calculating device 6 with reference to the time axis of the graph. Therefore, the information on the current session of blood purification treatment and the frequent-occurrence time slot can be compared visually. Moreover, the display control device 7 according to the present embodiment is capable of displaying the frequent-occurrence time slot calculated by the calculating device 6 as a band graph represented with reference to the time axis. Therefore, the comparison between the information on the current session of blood purification treatment and the frequent-occurrence time slot can be made more smoothly and visually.

Furthermore, the blood purification system includes the input device 8 that accepts selective input of any of the plurality of particular incidents. Furthermore, the calculating device 6 calculates the frequent-occurrence time slot of the particular incident inputted through the input device 8. Therefore, the frequent-occurrence time slot of any desired particular incident can be selectively displayed. In a case where a plurality of particular incidents are inputted through the input device 8, the display control device 7 may display the frequent-occurrence time slots of the plurality of particular incidents such that the kinds thereof are identifiable. Therefore, the frequent-occurrence time slots of a plurality of desired particular incidents can be displayed simultaneously. Furthermore, the display control device 7 according to the present embodiment may display the frequent-occurrence time slots such that the frequencies of occurrence of the respective particular incidents are identifiable. Therefore, an action suitable for the frequency of occurrence of each of the particular incidents can be taken.

Now, a second embodiment of the present invention will be described.

Figure 9:
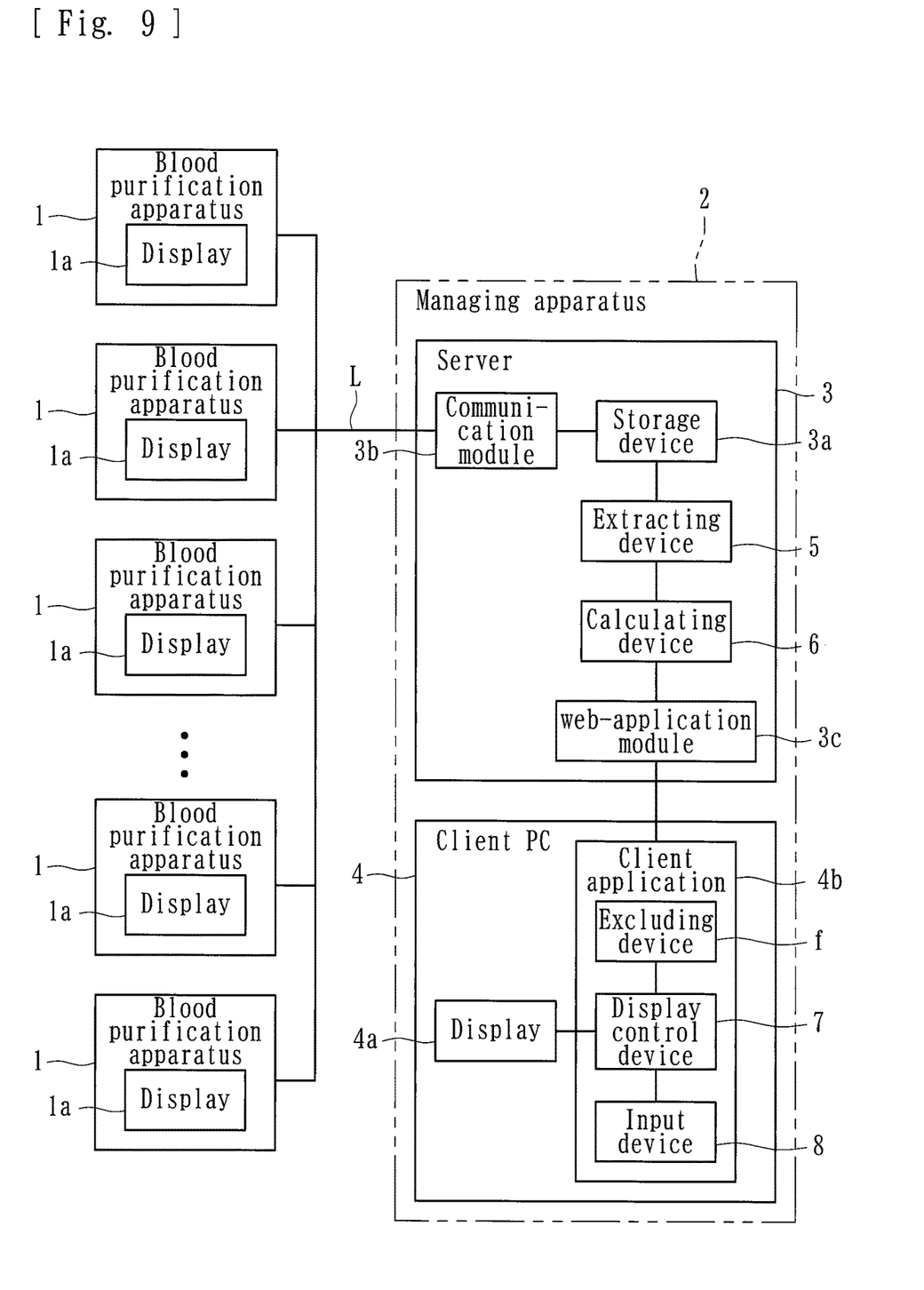
FIG. 9 is a block diagram of a blood purification system according to a second embodiment of the present invention.

As with the case of the first embodiment, a blood purification system according to the present embodiment is capable of giving dialysis treatment as blood purification treatment to patients and includes, as illustrated in FIG. 9, blood purification apparatuses 1 and a managing apparatus 2. The blood purification apparatuses 1 and the managing apparatus 2 are electrically connected to each other through LAN cables (L). Hence, the blood purification apparatuses 1 and the managing apparatus 2 can communicate with each other in such a manner as to transmit and receive information on the blood purification treatment to and from each other. Elements that are the same as those described in the first embodiment are denoted by corresponding ones of the reference numerals, and detailed description of such elements is omitted.

The client application 4b of the managing apparatus 2 according to the present embodiment includes an excluding device (f). The excluding device (f) is capable of excluding any of the histories accumulated in the storage device 3a from the object of search to be performed by the extracting device 5. Hence, the extracting device 5 according to the present embodiment can extract a particular incident by searching histories accumulated in the storage device 3a except those excluded by the excluding device (f).

The excluding device (f) according to the present embodiment allows the medical worker or the like to select and specify any history to be excluded from the object of search (i.e. from the histories accumulated in the storage device 3a) by, for example, checking or unchecking relevant checkboxes on the client application 4b. Exemplary items to be excluded by the excluding device f include histories except those of the current patient who is going to take blood purification treatment, patients other than the current patient and of a different sex or different ages, patients not having the same or a similar primary disease, patients not having the same or a close DW (dry weight) or test value, and so forth.

The excluding device (f) may be configured such that items to be excluded from the object of search performed by the extracting device 5 can be specified on the history basis. In such a case, the entirety of the history of a single treatment session can be excluded from the object of search. Hence, information that is unfavorable for performing highly accurate extraction can be excluded by units of treatment session. Furthermore, the excluding device (f) is capable of excluding any specified kind of data included in the histories (in the present embodiment, any specified kind of particular incident) from the object of search. In such a case, the object of exclusion can be specified more precisely. In addition to the exclusion on the basis of the kind of data, exclusion on the basis of treatment date or the like is also possible. In such a case, the object of exclusion may be specified on a matrix screen.

According to the present embodiment, the blood purification system includes the extracting device 5 capable of searching for and extracting any history satisfying a predetermined condition from among the histories accumulated in the storage device 3a, the excluding device (f) capable of excluding any of the histories accumulated in the storage device 3a from the object of search performed by the extracting device 5, and the display control device 7 capable of displaying various pieces of information based on the history extracted by the extracting device 5 on the display 4a. Therefore, any information that is unfavorable as the information to be extracted by the extracting device 5 can be excluded from the information accumulated in the storage device 3a. Hence, information necessary for the medical worker can be accurately displayed and grasped by the medical worker.

For example, if an action that is being taken in response to a warning generated by the blood purification apparatus 1 is inappropriate, the warning may be generated repeatedly. In such a case, although it should be recorded that a particular incident (generation of a warning) has occurred once, it is actually recorded in the history that the particular incident has occurred the number of times of repetition. To avoid such a situation, if the second and subsequent occurrences of the particular incident are excluded by the excluding device f, the extraction by the extracting device 5 can be performed accurately. Consequently, the reliability of the frequent-occurrence time slot to be displayed can be increased.

While some embodiments have been described above, the present invention is not limited thereto and may be connected to the server 3 of the managing apparatus 2 without using wires such as the LAN cables (L) (for example, the blood purification apparatuses 1 and the server 3 may be capable of wireless communication with each other). Moreover, the server 3 of the managing apparatus 2 that is connected to the blood purification apparatuses 1 may also be connected to any other independent server installed in a room other than the room related to dialysis treatment (for example, to a server included in any of various systems such as a system storing treatment information (electronic medical charts) and medication information of any other department in the same hospital (in a room different from the dialysis room, such as a room of an internal medicine concerning complications), a nursing support system provided for the nursing of patients, or a reservation or accounting system), so that the server 3 and the other server can transmit and receive various pieces of patient information to and from each other.

The display control device 7 according to each of the above embodiments is capable of displaying the frequent-occurrence time slot calculated by the calculating device 6 on the display 4a of the client PC 4 during the current session of blood purification treatment. Alternatively, the display control device 7 may display the frequent-occurrence time slot calculated by the calculating device 6 on the display 1a of a corresponding one of the blood purification apparatuses 1 during the current session of blood purification treatment. Furthermore, while each of the above embodiments concerns a case where the web-application module 3c for activating the client application 4b is provided in the server 3, the web-application module 3c may alternatively be provided in the client PC 4.

The above embodiments each concern a hemodialysis apparatus capable of performing a treatment such as hemodialysis (HD), ECUM, or HDF (hemodiafiltration). Alternatively, the present invention may be applied to a blood purification apparatus capable of performing another kind of blood purification treatment (such as hemofiltration (HF), continuous slow hemofiltration (CHF), or the like).

The present invention is applicable to any blood purification system, including those having other additional functions and so forth, as long as the following are satisfied: a history includes particular incidents having occurred unsteadily in the blood purification treatment, and the blood purification system includes an extracting device capable of searching the histories accumulated in the storage device and extracting a desired one of the particular incidents; a calculating device capable of calculating a time when the particular incident extracted by the extracting device occurs a predetermined or more number of times as a frequent-occurrence time slot; and a display control device capable of displaying the frequent-occurrence time slot calculated by the calculating device on a display during a current session of blood purification treatment.

REFERENCE SIGN LIST 1 blood purification apparatus
1a display
2 managing apparatus
3 server
3a storage device 3b communication module
3c web-application module
4 client PC
4a display
5 extracting device
6 calculating device
7 display control device
8 input device
9 blood circuit
10 blood pump
11 dialyzer (blood purifier)
12 duplex pump
13 ultrafiltration pump
14 external indicator lamp
R frequent-occurrence time slot
f excluding device

The invention claimed is:

1. A blood purification system comprising: a blood purification apparatus that provides blood purification treatment to a patient, the blood purification apparatus comprising: a speaker or an external indicator lamp that generates warning notifications; a managing apparatus that communicates with the blood purification apparatus in such a manner as to transmit and receive information on the blood purification treatment to and from the blood purification apparatus, the managing apparatus comprising: a server comprising: a storage device that stores the information about the blood purification treatment, of the patient, in a time course with progress of the blood purification treatment and accumulates the information as a history for each of the blood purification treatment sessions within the storage device as histories of a plurality of the blood purification treatment sessions, wherein the histories includes particular incidents having occurred unsteadily in the blood purification treatment include unsteady incidents related to behavior of the patient during the blood purification treatment or unsteady incidents related to a condition of the patient, and unsteady incidents occurring in the blood purification apparatus during the blood purification treatment; an extracting device that searches the histories accumulated in the storage device and extracting a desired type of the particular incidents stored on the storage device; a calculating device that calculates a time when the one of the particular incidents extracted by the extracting device occurs in a frequent-occurrence time slot a predetermined number of times or a number of times or more; and a client personal computer comprising: a display provided to the blood purification apparatus or to the managing apparatus that displays the information on the blood purification treatment, and a client application comprising: a display control device that displays pieces of the information on a current session of the blood purification treatment with a progress of the time course, and the display control device displays the frequent-occurrence time slot calculated by the calculating device on the display according to the progress of the time during the current session of the blood purification treatment; and an input device, wherein the frequent-occurrence time slot of one of the particular incidents is inputted through the input device can be calculated by the calculating device; wherein unsteady incidents include actions taken in response to warnings and notifications generated by the speaker or the external indicator lamp, wherein the display control device is capable of displaying information on the current session of blood purification treatment as a graph with progress of time, and is capable of displaying the frequent-occurrence time slot calculated by the calculating device with reference to a time axis of the graph; and wherein the display control device is capable of displaying the frequent-occurrence time slot calculated by the calculating device as a band graph with reference to the time axis.

2. The blood purification system according to claim 1, wherein the particular incidents include a first unsteady incident related to a patient's behavior during the blood purification treatment or a second unsteady incident related to a patient's condition, or a third unsteady incident occurring in the blood purification apparatus during the blood purification treatment.

3. The blood purification system according to claim 1, wherein the input device accepts a selective input of any of the particular incidents.

4. The blood purification system according to claim 3, wherein in a case where the particular incidents are inputted through the input device, the display control device is capable of displaying the frequent-occurrence time slots of the particular incidents such that kinds of the particular incidents are identifiable.

5. The blood purification system according to claim 1, wherein the display control device is capable of displaying the frequent-occurrence time slot such that a frequency of occurrence of the particular incident is identifiable.

6. The blood purification system according to claim 2, wherein the display control device is capable of displaying information on the current session of blood purification treatment as a graph with progress of time, and is capable of displaying the frequent-occurrence time slot calculated by the calculating device with reference to a time axis of the graph.

7. The blood purification system according to claim 2, wherein the input device accepts a selective input of any of the particular incidents.

8. The blood purification system according to claim 5, wherein the input device accepts a selective input of any of the particular incidents.

9. The blood purification system according to claim 6, wherein the input device accepts a selective input of any of the particular incidents.

10. The blood purification system according to claim 2, wherein the display control device is capable of displaying the frequent-occurrence time slot such that a frequency of occurrence of the particular incident is identifiable.

11. The blood purification system according to claim 8, wherein the display control device is capable of displaying the frequent-occurrence time slot such that a frequency of occurrence of the particular incident is identifiable.

12. The blood purification system according to claim 9, wherein the display control device is capable of displaying the frequent-occurrence time slot such that a frequency of occurrence of the particular incident is identifiable.

13. The blood purification system according to claim 3, wherein the display control device is capable of displaying the frequent-occurrence time slot such that a frequency of occurrence of the particular incident is identifiable.

14. The blood purification system according to claim 4, wherein the display control device is capable of displaying the frequent-occurrence time slot such that a frequency of occurrence of the particular incident is identifiable.

15. The blood purification system according to claim 1, wherein the information on the blood purification treatment that is displayed on the display includes a setting value represented by a flow rate of a blood pump, a setting value represented by a flow rate of an ultrafiltration pump, a setting value represented by a flow rate of an infusion pump, a venous pressure detected by a venous pressure sensor, or a hematocrit value detected by a hematocrit sensor.

16. The blood purification system according to claim 1, wherein the blood purification system is connected to and in communication with the managing apparatus and a computing unit, and the calculating device is part of the managing apparatus and the extracting device is part of the managing apparatus.

17. The blood purification system according to claim 1, wherein the extracting device extracts the particular incident in the histories of the patient to whom the blood purification treatment is going to be given.

18. The blood purification system according to claim 1, wherein the server is in communication with a plurality of blood purification apparatuses so that a plurality of users associated with each of the plurality of blood purification apparatus can references the histories stored on the storage device.

* * * * *